United States Patent [19]
Schnaibel et al.

[11] Patent Number: 6,073,083
[45] Date of Patent: Jun. 6, 2000

[54] ARRANGEMENT FOR DETERMINING THE INTERNAL RESISTANCE OF A LAMBDA PROBE

[75] Inventors: Eberhard Schnaibel, Hemmingen; Erich Junginger, Stuttgart; Lothar Raff, Remseck, all of Germany

[73] Assignee: Robert Bosch GmbH, Stuttgart, Germany

[21] Appl. No.: 08/923,966

[22] Filed: Sep. 5, 1997

[30] Foreign Application Priority Data

Sep. 6, 1996 [DE] Germany .................. 196 36 226

[51] Int. Cl.[7] ............................ G01R 27/00
[52] U.S. Cl. ............... 702/65; 702/64; 702/116; 324/691
[58] Field of Search ............ 702/65, 22–24, 702/30–32, 57, 64, 86, 99, 109, 116, 130, 133, 79, 176, 182–184, 189, FOR 104–106, FOR 156–158; 701/108, 109; 73/118.1, 118.2, 1.34, 23.36, 35.04–35.07; 123/688, 689, 691, 693–697; 422/82.02, 83, 98; 60/276, 277, 285, 274; 324/522, 525, 549, 691, 754, 755, 759, 760; 364/528.35; 700/299, 300

[56] References Cited

U.S. PATENT DOCUMENTS

| | | | |
|---|---|---|---|
| 5,140,535 | 8/1992 | Raff et al. | 702/104 |
| 5,224,345 | 7/1993 | Schnaibel et al. | 60/274 |
| 5,291,417 | 3/1994 | Schnaibel et al. | 364/528.35 |
| 5,375,415 | 12/1994 | Hamburg et al. | 123/691 |
| 5,392,643 | 2/1995 | O'Kennedy et al. | 73/118.1 |
| 5,692,487 | 12/1997 | Schuerz et al. | 123/696 |

*Primary Examiner*—Hal Wachsman
*Attorney, Agent, or Firm*—Walter Ottesen

[57] ABSTRACT

The invention is directed to an arrangement for determining the internal resistance of a lambda probe having a positive pole and an internal resistance. A computer includes at least one computer port having a switchable state, a signal input and fixed pregiven values. A supply voltage source having a positive pole and a measurement resistor are also provided. The positive pole of the supply voltage source is connected to the positive pole of the lambda probe via the computer port and the measurement resistor. An analog/digital converter is connected forward of the signal input and the positive pole of the lambda probe is connected directly to the analog/digital converter for applying variable values to the signal input via the analog/digital converter. The computer is adapted to compute the internal resistance of the lambda probe from the variable values applied to the signal input and the fixed pregiven values. A method of determining the internal resistance of a lambda probe is also disclosed.

8 Claims, 4 Drawing Sheets

ARRANGEMENT FOR DETERMINING THE INTERNAL RESISTANCE OF A LAMBDA PROBE

FIELD OF THE INVENTION

The invention relates to an arrangement for determining the internal resistance of a lambda probe of the Nernst type. The invention also relates to a method for determining the internal resistance of a lambda probe.

BACKGROUND OF THE INVENTION

The internal resistance of a lambda probe is significantly influenced by its temperature and can therefore be applied as a substitute quantity for the probe temperature. The knowledge of the probe temperature is useful for several purposes. The knowledge of the probe temperature permits, inter alia, a diagnosis of the probe heater as is required, for example, by the California Environmental Authority (CARB). Various methods for determining the internal resistance are already known. One known method provides impressing an alternating current signal on the probe which distinguishes from the probe use signal with respect to frequency so that both signal components can be separated by frequency filtering. The amplitude of the alternating-current signal obtained with filtering is dependent upon the temperature of the probe and therefore upon the internal resistance and is therefore suitable as a substitute quantity for temperature.

U.S. Pat. No. 5,140,535 discloses an arrangement for determining the internal resistance of the probe by connecting the positive pole of the probe to ground in a clock pulsed manner via a measurement resistor. The signal is transmitted to a computer in both clocked phases via a preamplifier and the computer computes the internal resistance of the probe from the signal and known values of the circuit.

SUMMARY OF THE INVENTION

It is an object of the invention to provide an arrangement for measuring the internal resistance of the probe with a minimum configuration of hardware.

The arrangement of the invention is for determining the internal resistance of a lambda probe having a positive pole and an internal resistance. The arrangement includes: a computer including at least one computer port having a switchable state, a signal input and fixed pregiven values; a supply voltage source having a positive pole; a measurement resistor; the positive pole of the supply voltage source being connected to the positive pole of the lambda probe via the computer port and the measurement resistor; an analog/digital converter connected forward of the signal input; the positive pole of the lambda probe being connected directly to the analog/digital converter for applying variable values to the signal input via the analog/digital converter; and, the computer being adapted to compute the internal resistance of the lambda probe from the variable values applied to the signal input and the fixed pregiven values.

In the ideal case, for which the current, voltage and resistor values of the circuit are to be designed, a clocked connection of the probe positive pole to the positive pole of a supply voltage source is provided directly via a computer port without a switching transistor interposed therebetween.

The required additional hardware for determining the internal resistance is limited in this case to a measurement resistor which affords advantages with respect to the cost of the circuit.

It is especially advantageous not to connect the plus pole of the probe clocked to ground but to connect the plus pole of the probe to the plus pole of a supply voltage source. The plus pole of the probe is formed by the electrode facing toward the reference gas; whereas, the minus pole is realized by the electrode facing toward the exhaust gas. For probes with a pumped reference, the reference gas must be formed by pumping in oxygen. The positive pole of the probe is connected to the positive pole of the supply voltage for determining the internal resistance. In this way, the current, which flows for determining the internal resistance, functions at the same time as a pump current for maintaining the pumped reference atmosphere. The current is supported within the probe electrolyte by negative oxygen ions which are pumped to the plus pole, that is, from the exhaust gas to the reference atmosphere.

It is especially advantageous that, via a variation of the time raster, the determination of the internal resistance can be carried out, which determination is wanted for diagnostic purposes for probes having a pumped reference and an air reference as well as the clocked pump current control for the probes having a pumped reference. The diagnosis based on the arrangement of the invention is therefore usable for both probe types without a hardware change. Present day diagnostic concepts developed for probes having an air reference therefore do not have to be changed for a changeover of the probe type or have to be changed only marginally in the software area of the port drive, as may be required.

It is furthermore advantageous, and in the interest of a precise measurement, to fix the scanning time point, at which the probe voltage value is read in, with a tight tolerance.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
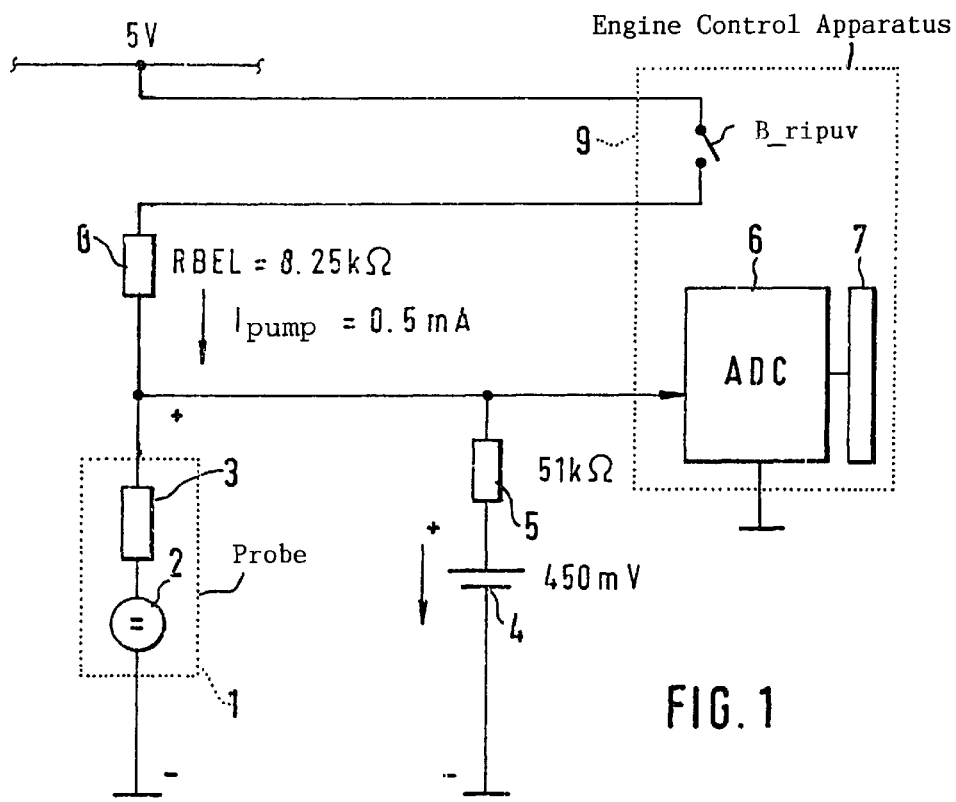
FIG. 1 is an electrical schematic of the arrangement according to the invention.
Figure 2:
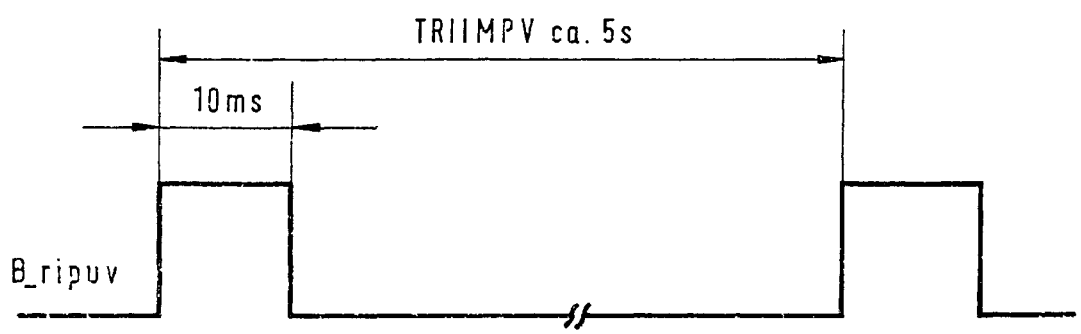
FIG. 2 is a plot of the computer internal signal B_ripuv shown as a function of time.

Reference numeral 1 identifies the equivalent circuit of an exhaust-gas probe having an emf voltage source 2, which supplies the Nernst voltage, and the internal resistance Ri (identified by reference numeral 3). A series circuit is connected in parallel with the probe. This series circuit includes a voltage source 4, which is approximately half the Nernst voltage of the probe (that is, supplies approximately 450 mV) and a resistor 5 which corresponds to approximately the value of the probe internal resistance at the start of operational readiness as a consequence of increasing warming of the probe. The plus pole of the probe is connected via an analog/digital converter 6 to a computer input 7. Furthermore, the plus pole is connected via a measurement or load resistor 8 (RBEL) and a computer port 9 to a supply voltage source of approximately 5 volts. The supply voltage and load resistance are so selected that a measurement current of 0.5 to 1 mA results. The computer port opens or closes the above-mentioned connection via the internal computer signal B_ripuv having a time-dependent trace as shown in FIG. 2 by way of example. The computer port 9 is closed every 3 to 5 seconds for a time duration of approximately 5 to 20 ms. Thereafter, the connection via the port is periodically closed every 5 seconds for a duration of 10 ms.

This time raster is based on the following. The detection of the probe signal takes place in a time raster of 10 ms. Accordingly, it is advantageous to make a load measurement every 3 to 5 seconds in that the computer port closes the above-mentioned connection for approximately 10 ms. With this time raster, the number of skipped regular measurements does not have a negative effect.

Figure 3:
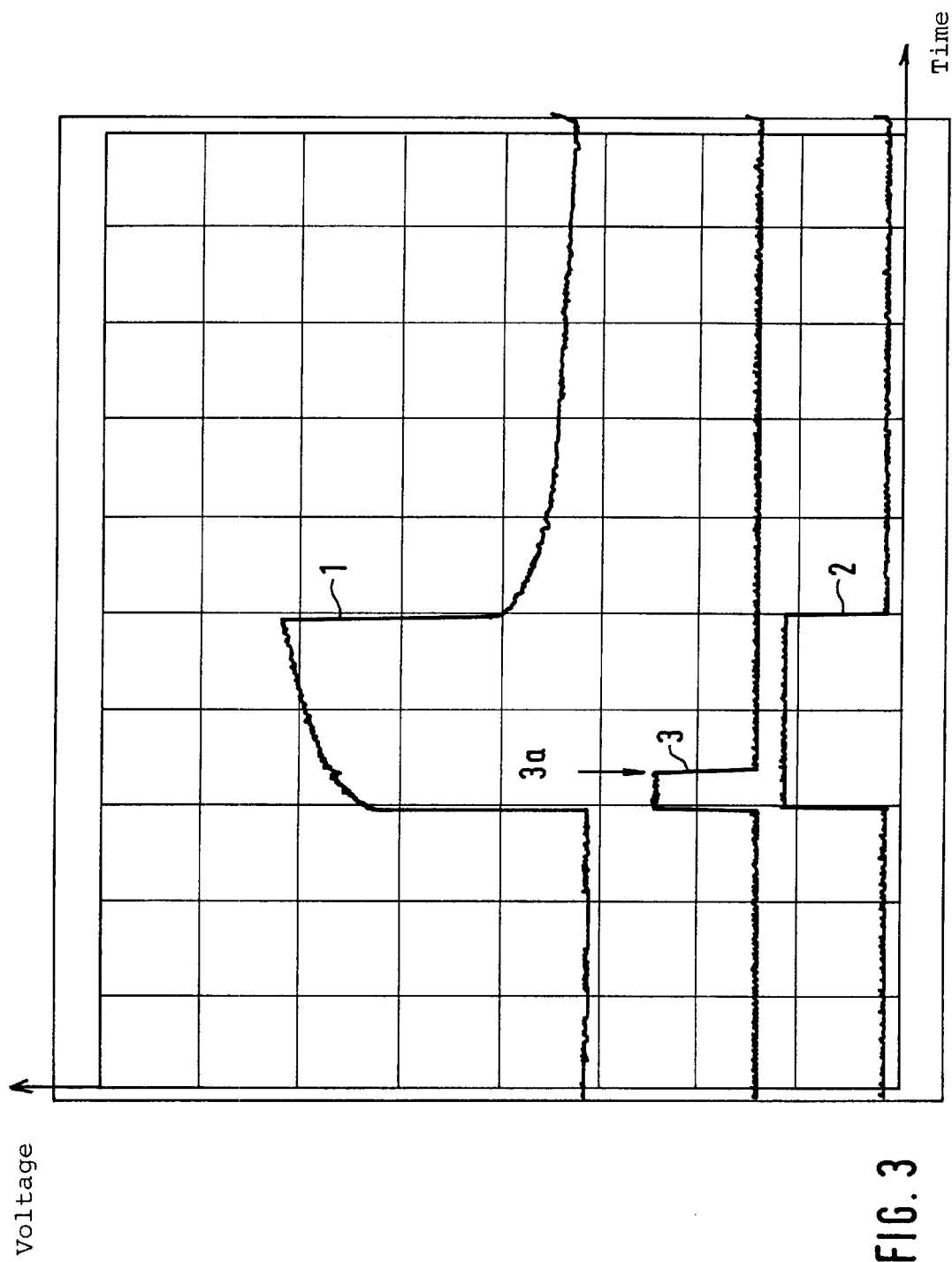
FIGS. 3 and 4 show time-correlated diagrams of the measurement and pump current pulses and the probe voltage corresponding thereto; and, FIG. 5 shows a probe having a pumped reference wherein the invention is especially advantageously realized.

FIG. 3 shows the voltage trace of the resulting probe voltage (curve 1) which is supplied to the analog/digital converter 6 together with the trace of the measurement pulses, load pulses or pump pulses (curve 2) and a curve 3 from which the measurement time point can be read. The values are recorded for a new probe at an internal resistance of 240 ohms. For the load because of the measurement pulse, curve 1 shows first an ohmic behavior in the form of a voltage jump and thereafter, a capacitive behavior which increases in accordance with an e-function. From this, it can be seen that the measuring time point has a considerable influence on the Ri statement depending upon whether the probe voltage value is read in near the start or near the end of the measuring pulse. In the interest of a precise measurement, it is therefore advantageous to determine within a tight tolerance the scanning time point 3a at which the probe voltage value is read in. Experiments have shown that a measurement time point of approximately 3 ms after the start of the test pulse is the best time point. The voltage of the lambda probe while loaded with a test pulse is read into the computer approximately 1 to 5 ms after the start of the test pulse.

Ideally, only the height of the proportional jump would have to be measured. This procedure is however not possible in actual operation because the probe signal is prefiltered as required for suppressing electromagnetic disturbance scatterings so that the oscillating time of this filtering must be allowed to elapse before the measurement value can be recorded.

Figure 4:
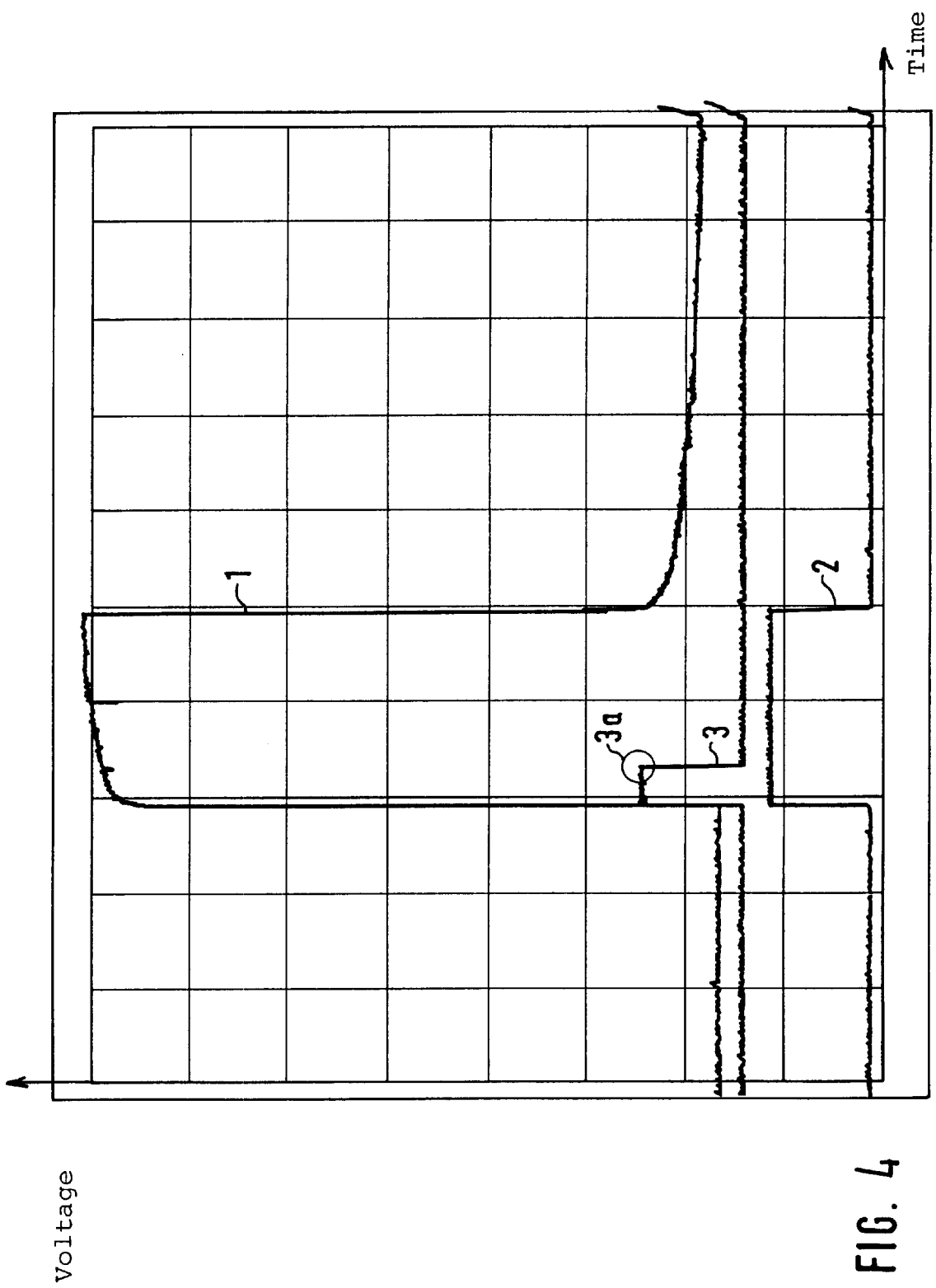

FIG. 4 shows the traces of FIG. 3 for a significantly higher internal resistance (2.4 kohm), that is, for an older probe.

From the two probe voltage curves, a recovery time is apparent which is needed by the probe after switch off of the measurement pulse in order to again obtain its previous potential. In view of the background of this repetitive effect, it can be advantageous to make no probe voltage measurements for approximately 30 ms or to correct these measurements as may be required.

The internal resistance to be determined is proportional to the product of the resistance RBEL and the quotient of the difference of the loaded and unloaded probe voltages in the counter and the difference of the supply voltage (for example, 5 volts) and the loaded probe voltage.

Figure 5:
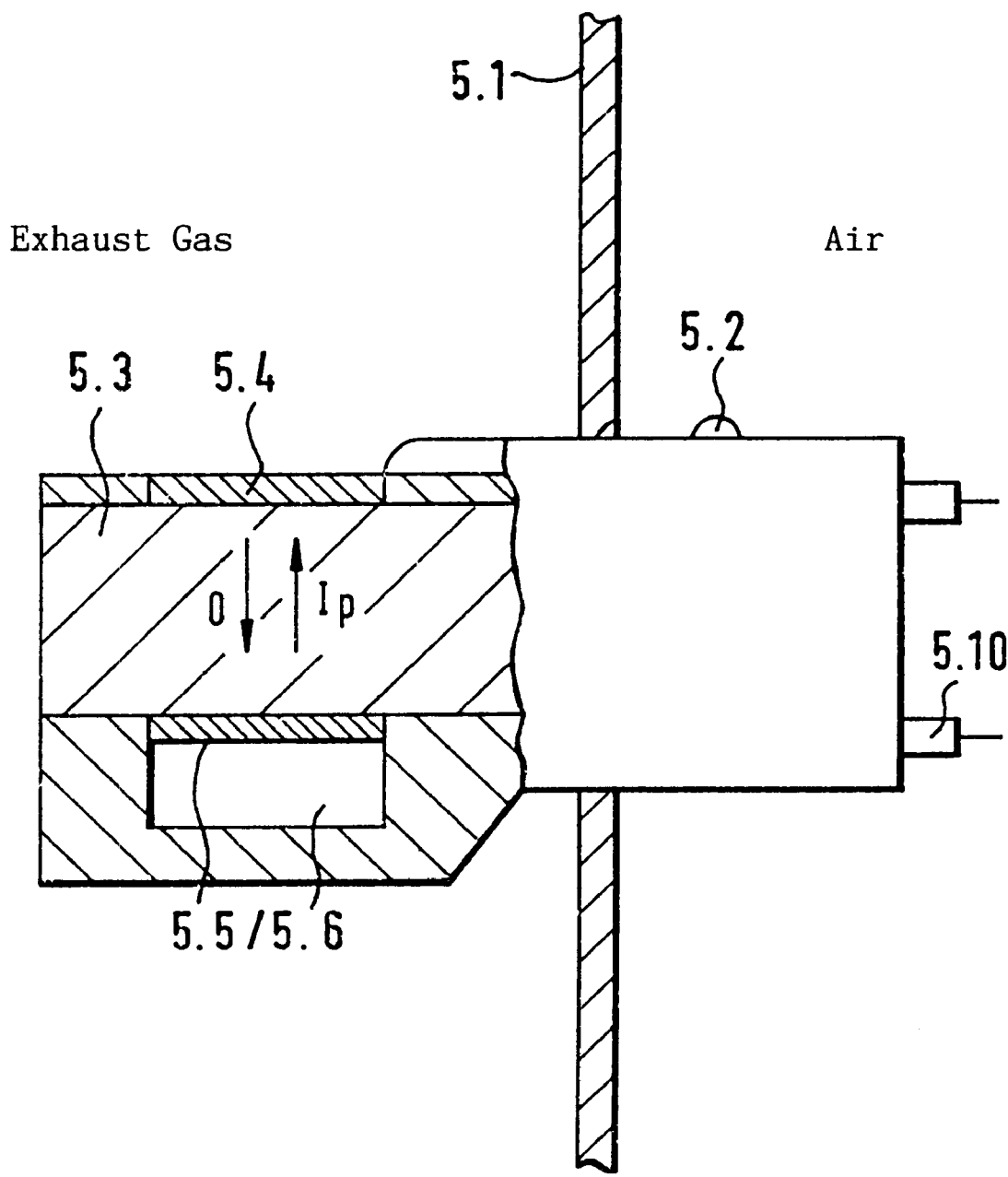

FIG. 5 shows a probe having a pumped reference as an example of an especially advantageous application of the invention.

FIG. 5 shows, in section, an exhaust-gas probe 5.2 in an exhaust-gas pipe of which a wall 5.1 is shown. This wall partitions the exhaust gas of an internal combustion engine (on the left) from the ambient air (on the right). In its exhaust-gas end portion, the exhaust-gas probe has a solid electrolyte 5.3 between a measurement electrode 5.4, which is subjected to the exhaust gas, and a reference electrode 5.5. A reference gas volume 5.6 communicates with the reference electrode 5.5 and is neither in direct contact with the exhaust gas nor the ambient air. An overpressure which possibly develops in the reference gas volume is reduced via an indirect connection to the ambient air such as via a porously configured measurement input line 5.10.

For maintaining a stable reference gas atmosphere, it is essential that the supply of oxygen via the pump current Ip exceeds, in time average, the occurring losses of oxygen. Such losses perforce occur from the measurement of the voltage US=Un when the voltage measurement is based on a current measurement via a measuring resistor. Typically, measurement resistors in the megohm range are used in the area of measuring voltages in the order of magnitude of an output voltage Un of an exhaust-gas probe of 1 volt. As a consequence, a measurement current flows in the microampere range. In the electrolyte, this current is supported by oxygen ions from the reference gas volume so that the oxygen concentration in the reference gas volume is reduced by the measurement.

The measurement pulse can have a height and a time-dependent width which are so dimensioned that it supplies the required pump current in time average. The computer port is opened and closed so as to cause a pump current of 10 to 50 mA in average.

A measuring pulse of 1 mA for 10 ms, which is provided every 200 ms, effects a time-averaged pump current of 25 mA which is adequate for typical motor vehicle applications. The computer port is closed approximately every 200 ms for a time duration of 5 to 20 ms.

It is understood that the foregoing description is that of the preferred embodiments of the invention and that various changes and modifications may be made thereto without departing from the spirit and scope of the invention as defined in the appended claims.

What is claimed is:

1. An arrangement for determining the internal resistance of a lambda probe having a positive pole and an internal resistance, the arrangement comprising:

a computer having a signal input and including a computer port for outputting digital signals;

a supply voltage source having a positive pole;

a measurement resistor;

said positive pole of said supply voltage source being connected to said positive pole of said lambda probe via said computer port and said measurement resistor;

said computer having fixed pregiven values associated therewith and said fixed pregiven values including the value of said supply voltage and the value of said measurement resistor;

an analog/digital converter connected forward of said signal input;

said positive pole of said lambda probe being connected directly to said analog/digital converter for applying varying voltages of said lambda probe to said analog/digital converter and, after processing in said analog/digital converter, to said signal input;

said computer being adapted to compute said internal resistance of said lambda probe from said varying voltages applied to said signal input and said fixed pregiven values;

said computer port having a switching rate;

said computer including means for periodically changing said switching rate in a pregiven time raster so that the connection of said positive pole of said supply voltage source and said lambda probe are periodically opened and closed;

a series circuit including a ancillary voltage source and a ancillary resistor;

said series circuit being connected in parallel with said lambda probe; and, said ancillary voltage source being a source voltage corresponding to approximately half of the Nernst voltage of said lambda probe and said ancillary resistor corresponding to approximately half the value of said internal resistance when said lambda probe is operationally warm.

2. The arrangement of claim 1, wherein said supply voltage source and said measurement resistor are so selected that a measurement current of 0.5 to 1 mA results.

3. The arrangement of claim 1, wherein said computer includes means for closing said computer port every 3 to 5 seconds for a time duration of approximately 5 to 20 ms.

4. The arrangement of claim 1, wherein said lambda probe has a pumped reference gas atmosphere; and, said computer including means for controlling said computer port so that the duration of a load pulse is adequate for a clocked resupply of oxygen to the pumped reference gas atmosphere.

5. The arrangement of claim 4, said means for controlling said computer port being adapted to open and close said computer port so as to cause a pump current of 10 to 50 $\mu$A on average.

6. The arrangement of claim 5, wherein said computer port is closed approximately every 200 ms for a time duration of 5 to 20 ms.

7. The arrangement of claim 1, wherein said lambda probe can be loaded with a test pulse; and, said computer comprising means for computing the internal resistance of the lambda probe as proportional to the product of the resistance of said measurement resistor and the quotient of the difference of the voltage of said lambda probe loaded and not loaded by said test pulse and the difference of the supply voltage and the voltage of said lambda probe loaded by said test pulse.

8. The arrangement of claim 7, wherein the voltage of said lambda probe while loaded with a test pulse is read into said computer approximately 1 to 5 ms after the start of the test pulse.

* * * * *